(12) United States Patent
Kauffman

(10) Patent No.: US 7,927,877 B1
(45) Date of Patent: Apr. 19, 2011

(54) DETECTION AND ANALYSIS OF BIODIESEL IN FUELS

(75) Inventor: Robert E. Kauffman, Centerville, OH (US)

(73) Assignee: Herguth Technologies, Inc., Vallejo, CA (US)

( * ) Notice: Subject to any disclaimer, the term of this patent is extended or adjusted under 35 U.S.C. 154(b) by 236 days.

(21) Appl. No.: 12/286,845

(22) Filed: Oct. 1, 2008

Related U.S. Application Data

(60) Provisional application No. 60/976,726, filed on Oct. 1, 2007.

(51) Int. Cl.
*G01N 31/00* (2006.01)

(52) U.S. Cl. .......................................... 436/60; 436/164
(58) Field of Classification Search ................... 436/60, 436/164
See application file for complete search history.

*Primary Examiner* — Jill Warden
*Assistant Examiner* — Dwan A Gerido
(74) *Attorney, Agent, or Firm* — Christensen O'Connor Johnson Kindness PLLC

(57) ABSTRACT

A method of analyzing biodiesel content in a fuel sample generally includes providing a fuel sample including at least one of a biodiesel and other diesel fuel; mixing a predetermined amount of solvent to the fuel sample, wherein the fuel sample is soluble in the solvent; mixing a predetermined amount of water to the fuel sample; analyzing the fuel sample for a change; and associating the change with a biodiesel content in the fuel sample.

17 Claims, 12 Drawing Sheets
(11 of 12 Drawing Sheet(s) Filed in Color)

Glass Tube with Graduations Corresponding to Biodiesel Fuel Concentration

Fuel Solubility in 3 mL of Denatured Ethanol Containing 2.5% Distilled Water

Permanganate Fuel Test in 3 mL of Denatured Ethanol Containing 2.5% Distilled Water – Shaking 2 Seconds Saponification Biofuel Test Using Phenolphthalein in Aqueous Basic Denatured Alcohol

DETECTION AND ANALYSIS OF BIODIESEL IN FUELS

CROSS-REFERENCE TO RELATED APPLICATION

This application claims the benefit of U.S. Provisional Patent Application No. 60/976,726, filed Oct. 1, 2007, the disclosure of which is hereby expressly incorporated by reference.

BACKGROUND

Biodiesel fuels are mono-alkyl (e.g., methyl) esters of long chain fatty acids derived through saponification of the glycerol triesters of vegetable oils and animal fats. When used "straight," the biodiesel fuel is referred to as "B100". When blended into ultra low sulfur diesel (ULSD, having below 15 ppm sulfur content) or other petroleum-based diesel fuels, the blended fuel is named according to its percentage of biodiesel concentration. For example, fuel containing 20% biodiesel is referred to as "B20" and fuel containing 10% biodiesel is referred to as "B10". Due to possible stability and performance issues, diesel engine operators are in need of an on-site test which can quickly quantify the percentage of biodiesel in fuel stores prior to fueling operations.

On-site testing is important in the biodiesel fuel industry because different customers desire a quantitative analysis of fuels before using the fuels. For example, nuclear power plants desire little to no biodiesel in their diesel fuels. However, the trucking industry does want biodiesel in their ULSD fuels to reduce environmental contaminants. Further complicating the situation, a large number of the nuclear power plants do not use ULSD fuels, but rather still use non-ULSD diesel fuels (such as low sulfur and regular sulfur diesel fuels) having a higher sulfur content (up to 400 ppm sulfur for low sulfur fuel and up to 1500 ppm for regular sulfur diesel fuel), as well as other easily oxidizable compounds, such as phenols, amines, and unsaturated molecules.

Although analytical techniques based on gas chromatography (GC) and Fourier transform infrared (FTIR) spectrophotometry have been used successfully to measure the percentage of biodiesel in ULSD and other non-ULSD diesel fuels, they are not suitable for on-site analyses. Moreover, other compounds present in ULSD, such as carboxylic acids, hydroperoxides, etc., limit the detection capabilities of the GC and FTIR techniques of biodiesel fuel concentrations that are below about 2% of the total fuel. Therefore, there exists a need for a simple, accurate, on-site biodiesel concentration quantification test for blended biodiesel and ULSD or other non-ULSD diesel fuels.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In accordance with one embodiment of the present disclosure, a method of analyzing biodiesel content in a fuel sample is provided. The method generally includes providing a fuel sample including at least one of a biodiesel and other diesel fuel, and mixing a predetermined amount of solvent to the fuel sample, wherein the fuel sample is soluble in the solvent. The method further includes mixing a predetermined amount of water to the fuel sample. The method further includes analyzing the fuel sample for a change and associating the change with a biodiesel content in the fuel sample.

In accordance with another embodiment of the present disclosure, a method of analyzing biodiesel content in a fuel sample is provided. The method generally includes providing a fuel sample including at least one of a biodiesel fuel and other diesel fuel, and adding a predetermined amount of solvent to the fuel sample, wherein the fuel sample is soluble in the solvent. The method further includes adding a predetermined amount of water to the fuel sample, and adding a predetermined amount of potassium permanganate to the fuel sample. The method further includes analyzing the fuel sample for a change and associating the change of the fuel sample with a biodiesel content.

In accordance with another embodiment of the present disclosure, a method of analyzing biodiesel content in a fuel sample is provided. The method generally includes providing a fuel sample including at least one of biodiesel and one other fuel, and mixing an aqueous basic ethanol solution with the fuel sample, wherein the initial number of moles of basic alcohol solution is known, and wherein the basic alcohol solution reacts with the same number of moles of biodiesel. The method further includes titrating at least a portion of the reacted basic alcohol solution to an equivalence endpoint with an aqueous acidic alcohol solution containing hydrogen chloride to determine the remaining number of moles of basis alcohol solution and calculating the difference between the initial number of moles of basic alcohol solution and the remaining number of moles after reacting the basic alcohol solution with the fuel sample.

DESCRIPTION OF THE DRAWINGS

The patent or application file contains at least one drawing executed in color. Copies of this patent or patent application publication with color drawing(s) will be provided by the Office upon request and payment of the necessary fee.

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
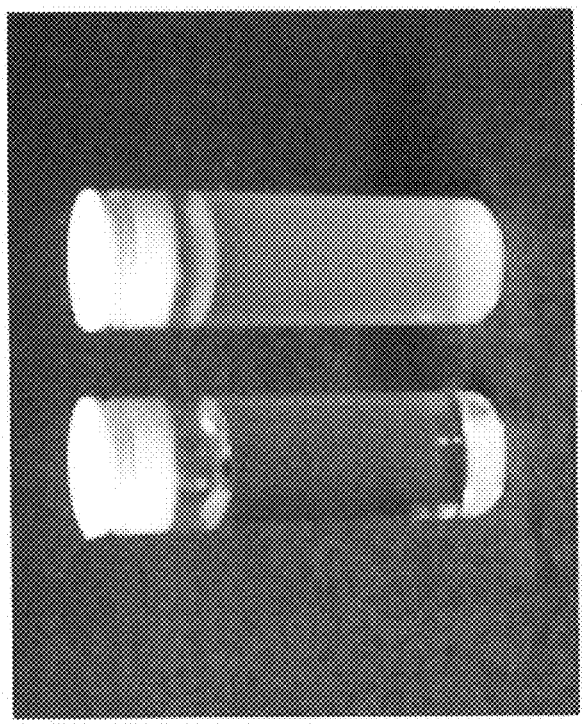
FIGS. 1-3 are photographic images of fuel samples being tested in accordance with one method of the present disclosure.

Simple wet chemistry techniques have been developed for on-site detection of biodiesel fuel in ULSD fuels. The concentration of biodiesel in the ULSD fuel can be determined by comparing fuel samples with standards using visual methods such as color charts and pictures or portable colorimeters. The developed techniques make use of the chemical differences between biodiesel and ULSD fuels, i.e., biodiesel fuels are methyl esters of unsaturated fatty acids, while ULSD fuels are branched alkyl/aromatic chains (for example, in the kerosene range) obtained through distillation of petroleum.

Three wet chemistry tests performed alone or in suitable succession can be used to identify and, if desired, quantify the presence of biodiesel in ULSD and other fuels. The three tests include the following: (1) solubility in an aqueous alcohol solution; (2) reaction with potassium permanganate in an aqueous alcohol solution; and (3) saponification in a basic, aqueous alcohol solution. These techniques may be used alone or in combined succession to determine the presence and quantity of biodiesel content in fuels.

Solubility Test

The test for solubility in an aqueous alcohol solution will now be described. Due to the ester linkage (O—C=O) in the alkyl esters of biodiesel fuels, biodiesel fuels have a higher affinity for water than diesel fuels (whether ULSD, low sulfur, or regular sulfur diesel fuels). Biodiesel fuel, diesel fuel, and water are all soluble in alcohols (e.g., higher than methanol, such as isopropanol (IPA)) as well as other lower molecular weight ketones (e.g., acetone), esters (e.g., ethyl acetate), carboxylic acids (e.g., acetic acid), and nitriles (e.g., benzonitrile). Accordingly, a solubility test has been developed based on the water affinity and organic solvent solubility differences between biodiesel and other diesel fuels, such as ULSD, low sulfur, and regular sulfur diesel fuels.

The method for the solubility test includes selecting a solvent in which both types of fuels are soluble, such as one selected from the group listed above including alcohols (e.g., higher than methanol) as well as other lower molecular weight ketones (e.g., acetone), esters (e.g., ethyl acetate), carboxylic acids (e.g., acetic acid), and nitriles (e.g., benzonitrile). A specific amount of solvent is mixed with a sample of the fuel. In addition, a specific amount of water is mixed with the solvent/fuel solution that will cause the diesel fuel to become insoluble (solution becomes hazy/cloudy) while the biodiesel remains soluble (solution clear). The amount of water added to the solvent is dependent on several factors, including the solvent selected, the solvent/fuel ratio, and the percent of biodiesel to be detected. It should be appreciated that differentiation between high sulfur and ULSD fuels having different biodiesel contents by using solvent ratios to control the rate of reaction is also within the scope of the present disclosure.

In one non-limiting example, a solvent to fuel ratio of about 6 parts denatured ethanol (including about 2.5% water) to about 1 part fuel can be used to differentiate between ULSD (cloudy) and B10 and greater (clear). In another non-limiting example, a solvent to fuel ratio of about 5 parts denatured ethanol (including about 2.5% water) to about 1 part fuel can be used to differentiate between B10 and greater (cloudy) and B20 and greater (clear). In another non-limiting example, a solvent to fuel ratio of about 9 parts denatured ethanol (including about 5% water) to about 1 part fuel can be used to differentiate between ULSD (cloudy) and B20 and greater (clear). In another non-limiting example, a solvent to fuel ratio of about 8 parts isopropanol (IPA) (including about 15% water) to about 1 part fuel can be used to differentiate between B0 and greater (cloudy) and B5 and greater (clear).

In accordance with one embodiment of the present disclosure, the method includes providing a fuel sample including at least one of a biodiesel and other diesel fuel, and mixing a predetermined amount of solvent to the fuel sample, wherein the fuel sample is soluble in the solvent. The method further includes mixing a predetermined amount of water with the fuel sample, visually analyzing the fuel sample to determine if the fuel sample changes, and associating the change with a biodiesel content in the fuel sample. In one embodiment of the present disclosure, the fuel sample will visually change from a clear solution to a cloudy solution after water is added to the fuel sample if less than a specific concentration of biodiesel fuel is present in the fuel sample.

As described in greater detail below, it should be appreciated that coloring, such as methylene blue (0.05%) in water can be added to the solvent and water mixture to add color to the test solution to make the solution cloudiness easier to observe. Other soluble dyes (e.g., Congo red, food color) may also be used to give the test solution color.

The following EXAMPLES 1-3 provide examples of specific tests using specific quantities of fuel and water, as well as specific quantities and types of solvents.

Example 1

In one example, 0.5 milliliters (mL) of two samples, ULSD fuel and B20 fuel, were pipetted into separate 5-mL glass vials. Into each vial, 3-mL of denatured ethanol (containing 5% methanol, 5% isopropanol, and 90% ethanol) containing 2.5% of distilled water was added. The two vials were capped and hand shaken for approximately 10 seconds. As FIG. 1 shows, the vial containing B20 was clear, while the ULSD fuel was cloudy. Additional tests found that all ULSD fuels containing a higher than 10% concentration of biodiesel (i.e., greater than B10, up to B100) produced clear solutions.

Example 2

Figure 2:
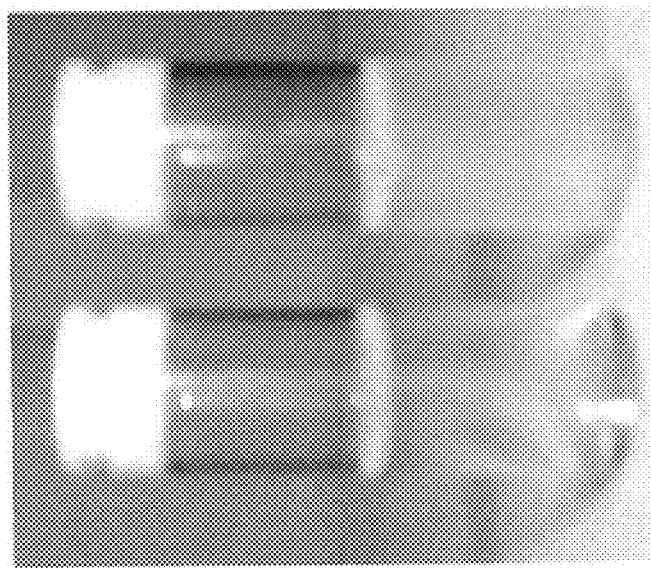

To differentiate between B10 and B20 fuels, the test was repeated using 2.5-mL of 2.5% water in denatured ethanol and 0.5-mL of fuel. As shown in FIG. 2, the B20 fuel produced a clear solution while the B10 fuel produced a cloudy solution.

Example 3

Figure 3:

In another example, 1-mL samples of ULSD fuel and B20 fuel were pipetted into separate 15-mL glass vials. Into each vial, 9-mL of denatured ethanol containing 5% of distilled water was added (e.g., vial filled to 10-mL line on vial in FIG. 3). As shown in FIG. 3, the B20 fuel solution was clear and the ULSD fuel solution was cloudy.

The examples illustrated in EXAMPLES 1-3 and respective FIGS. 1-3 demonstrate that the solubility test can easily differentiate between ULSD fuels containing different concentrations of biodiesel fuels by selecting the correct solvent, water, and fuel ratio. Therefore, if a known concentration of biodiesel is of interest (e.g., greater than B20, up to B100), then the required ratio of solvent, water, and fuel can be preselected. However, if the solubility test is being performed without a set limit, then a glass vial with multiple volume markings (see FIG. 4) can be used. In this case, the amount of fuel and concentration of water in the solvent are kept constant, while the amount of solvent is varied to determine the biodiesel concentration.

Figure 4:
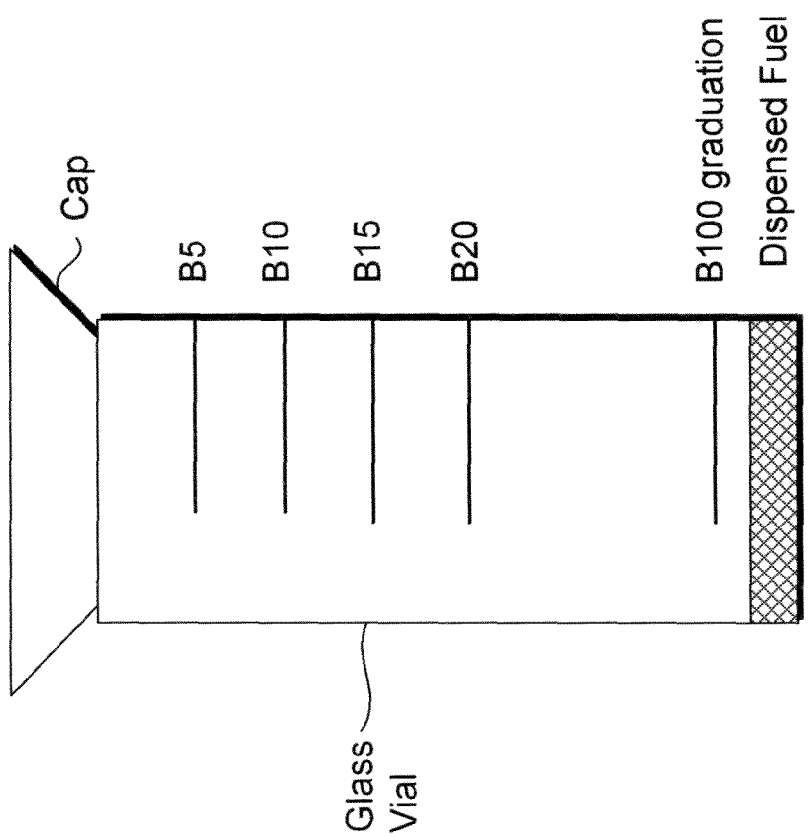
FIG. 4 is a front view of an apparatus for testing fuel samples in accordance with another method of the present disclosure.

As illustrated in FIG. 4, the vial includes several markings (i.e., B100, B20, B15, B10, and B5) that represent percentages of biodiesel in a fuel sample and relate to the volume of solvent added to the vial. The user dispenses a set amount of fuel into the vial. The user then pours the aqueous solvent solution into the vial to bring the fuel/solvent level up to the first mark, caps the vial, shakes by hand for 10 seconds, and then checks the produced solution for clarity. If the solution is clear, then the fuel is 100% biodiesel (B100). If the solution is cloudy, then the biodiesel content is less than 100%, and more solvent is added to the vial to bring the solution level up to the next graduation. The vial is capped, hand shaken for an additional 10 seconds, and then checked for clarity. If the solution is clear, then the fuel is 20% (B20) or above 20% biodiesel fuel.

The graduations can be adjusted to other concentrations between 20% (B20) and 100% (B100), but B20 was selected for FIG. 4 due to its presence in the current diesel fuel market. If the fuel is still cloudy, then successive aqueous solvent additions (raise the solvent/fuel level to the next graduation) to the vial, followed by shaking, can be performed to determine biodiesel concentrations between 20% (B20) and 5% (B5). As another non-limiting example, one large aqueous solvent addition can be made to confirm the biodiesel concentration is below 5%.

In another embodiment of the present disclosure, the fuel content may be varied in the vial, as opposed to the solvent content. In one non-limiting example, a vial may be provided with 0.2 mL of denatured ethanol (containing 2% water). Fuel may be added to the vial in an amount between about 0.5 mL about 2 mL. The vial is then shaken for 10 seconds and let to stand for 10 seconds. If the sample in the vial remains clear then the test indicates that the sample is B20 or greater. If the sample in the vial turns cloudy, then the sample is less than B20, and additional testing may be performed to further determine the content of biodiesel in the sample.

In the next step, additional fuel may be added to the test vial, such that total fuel content is in the range of about 8 mL to about 12 mL. The vial is then shaken for 10 seconds and let to stand for 10 seconds. If the sample in the vial remains clear then the test indicates that the sample is B10 or greater (i.e., between B10 and B20). If the sample in the vial turns cloudy, then the sample is less than B10, and additional testing may be performed to further determine the content of biodiesel in the sample.

In the next step, additional fuel may be added to the test vial, such that total fuel content is in the range of about 15 mL to less than about 17 mL. The vial is then shaken for 10 seconds and let to stand for 10 seconds. If the sample in the vial remains clear then the test indicates that the sample is B5 or greater (i.e., between B5 and B10). If the sample in the vial turns cloudy, then the sample is less than B5, and additional testing may be performed to further determine the content of biodiesel in the sample.

In the next step, additional fuel may be added to the test vial, such that total fuel content is in the range of greater than about 17 mL to less than about 19 mL. The vial is then shaken for 10 seconds and let to stand for 10 seconds. If the sample in the vial remains clear then the test indicates that the sample is B2 or greater (i.e., between B2 and B5). If the sample in the vial turns cloudy, then the sample is less than B2, and additional testing may be performed to further determine the content of biodiesel in the sample.

In the next step, additional fuel may be added to the test vial, such that total fuel content is in the range of more than about 19 mL. The vial is then shaken for 10 seconds and let to stand for 10 seconds. If the sample in the vial remains clear then the test indicates that the sample is B2 or less.

In one suitable embodiment of the present disclosure, a kit is provided, which includes a plurality of different vials including solvent and water solutions to which fuel samples are added. In each of the vials, either the solvent content or the fuel content may be varied to determine biodiesel content of the fuel sample. An exemplary kit includes five different vials for testing less than B2, B2 or greater, B5 or greater, B10 or greater, and B20 or greater, each vial including a specific amount of solvent, such as 0.2 mL of denatured ethanol (containing 2% water), to which different fuel amounts are added to determine the biodiesel content in the fuel, for example, as described above.

It should be appreciated that highly oxidized diesel fuels may have some interference near the lower limits of the test (e.g., below B5) depending on the solubility of the oxidation products in the aqueous ethanol. Accordingly, a wide range of water and solvent, such as isopropanol (IPA), solutions can be used effectively to determine the amount of biodiesel in the fuel at lower limits. As the water percentage increases, the amount of IPA solution used to differentiate between fuels can also be increased, for example, use 2 grams of 7.5% water in IPA solution or 4.75 grams of 12% water in IPA solution.

In some situations, it may be useful to determine whether a fuel is B5 or higher. For example, in the diesel fuel market, diesel fuels containing less than 5% biodiesel are generally designated as diesel (without a "B" prefix) and do not require additional fuel specification tests. Accordingly, it is desirable to easily identify B5 and higher biodiesel fuels using a set amount of aqueous alcohol solution with 1 mL of fuel. In one suitable B5 or higher test, isopropanol (IPA) can be used as the solvent, in place of denatured alcohol, and water can be increased to 15% of the solution to reduce the volatility and/or toxicity of solvent solution. Methylene blue (0.05%) in water can also be added to the solvent and water mixture to add color to make the insoluble droplets easier to observe. However, it should be appreciated that any water and IPA soluble dye (e.g., Congo red, food color) can be used to give the test solution color.

EXAMPLE 4 below provides an example of a specific test using IPA and water solution including methylene blue for analyzing B5 or higher biodiesel content in a fuel sample.

Example 4

Figure 5:
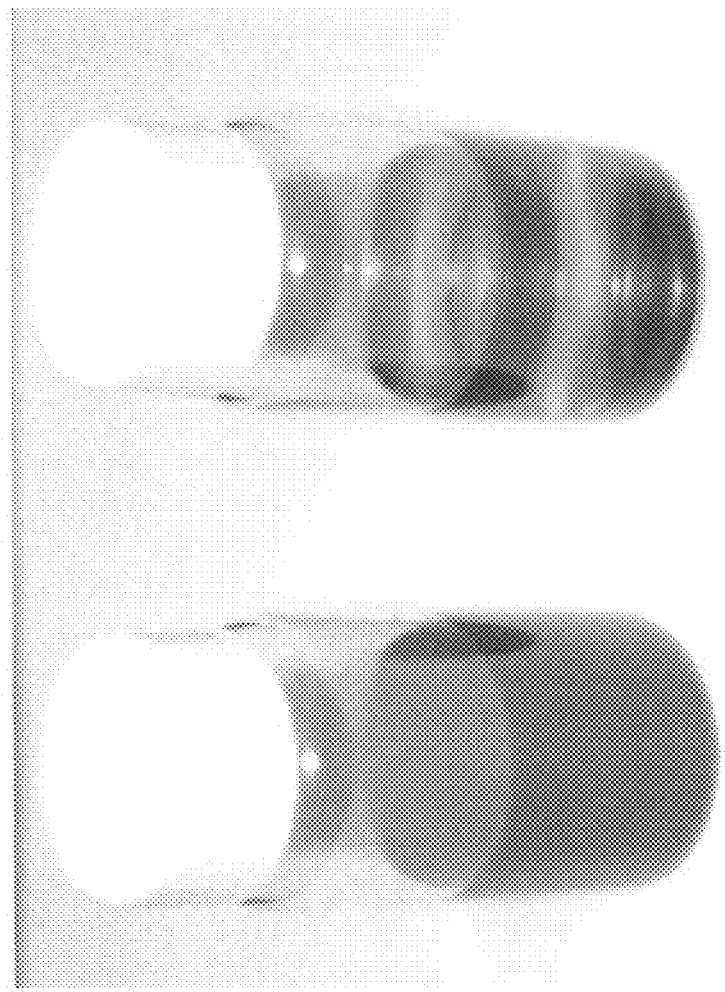
FIGS. 5-12 are photographic images of fuel samples being tested in accordance with other methods of the present disclosure.

An isopropanol (IPA) solution was made by combining 2 g of 0.05% methylene blue in water and 13 g of deionized water with 85 g of IPA (15% water). The IPA solution was weighed out into two 8 g portions and poured into two 25 mL glass vials. Into one vial, 1 mL of B0 diesel fuel was added. Into the other vial, 1 mL of B5 diesel fuel was added. The vials were closed and shaken for 5 seconds. As seen in the photographs shown in FIG. 5, B0 produced a cloudy, light blue solution, and B5 produced a clear, blue solution.

For very low biodiesel amounts in fuels, certified standard samples can be used for comparison because solubility parameters will be affected by test temperature. For example, if the test fuel is clear after testing, run B0 fuel to verify the result would be cloudy if biodiesel is not present. If the test fuel is cloudy after testing, run certified B1 or higher fuel to verify the result would be clear if biodiesel is present. In laboratory conditions, the inventors found that they were able to differentiate between B0 (cloudy/light blue) and B0.25 (0.25% biodiesel) (hazy/blue). In lieu of comparative standards, it should be appreciated that a heated block may be used to ensure consistent temperature parameters for all tests.

Reaction with Potassium Permanganate Test

The test for reacting with potassium permanganate in an aqueous alcohol solution or water solution will now be described. Although it should be appreciated that any of the solvents listed above for the solubility test could also be used for the potassium permanganate test, denatured alcohol is preferably used due to its beneficial effect on the reaction between potassium permanganate and alkenes (i.e., the Baeyer test for unsaturation, as evidenced by the presence of alkenes). In that regard, when ULSD and B20 fuels are dissolved in acetone and other polar organic solvents, the fuels undergo minimal reaction with potassium permanganate, and therefore the solutions remain purple for several minutes (the decolorization rate is independent of the fuel type). However, in denatured ethanol, B20 instantly decolorizes the potassium permanganate (turns yellow). Accordingly, in one embodiment of the present disclosure, the change to the fuel sample will be a change in color.

Water is also a suitable aqueous medium for the potassium permanganate test. Ethanol is generally preferred over water because it allows the solubility test to be performed in the same vial as the permanganate test. In that regard, ULSD, B100, and B20 fuels are all insoluble in water, negating the solubility test when water is used for the potassium permanganate test.

As a non-limiting example of a combined solubility/potassium permanganate test in accordance with the present disclosure, both tests are performed in the same vial. In that regard, ethanol is added to a fuel sample in a vial to check for clarity, then permanganate is added to the same vial to further test fuel for permanganate reactivity (i.e., the presence of unsaturation due to the presence of biodiesel in the fuel mixture). As another non-limiting example, two vials are used—one for solubility with ethanol and the other for permanganate reactivity with water.

The potassium permanganate test is preferably used for biodiesel and/or ULSD fuel mixtures because the oxidizable species in low sulfur and regular sulfur diesel fuels will react with the potassium permanganate, as described in U.S. Patent Application Publication No. 2008/0165361 A1, to Kauffman, filed on Jan. 4, 2008, the disclosure of which is hereby expressly incorporated by reference. Accordingly, oxidizable species in low sulfur and regular sulfur diesel fuels will give a false positive reading for biodiesel content. Accordingly, in one suitable embodiment of the present disclosure, the potassium permanganate test can be used in combination with the solubility test to determine, first, fuel contamination, either by oxidizable species or by biodiesel present in the fuel, using the potassium permanganate test; and second, the presence and/or concentration of biodiesel in the fuel using the solubility test. This two-part test is particularly suitable for analyzing fuels used in diesel trucks for which ULSD fuel use is mandated and biodiesel content is preferred.

In one non-limiting example, a solvent to fuel ratio of 6 parts denatured ethanol (including 2.5% water) to 1 part fuel can be used to differentiate between ULSD (purple) and B20 (decolorized/yellow) with 1/20 part of 0.5% potassium permanganate. In another non-limiting example, a solvent to fuel ratio of 6 parts water to 1 part fuel can be used to differentiate between ULSD (pink) and B20 (lighter pink) with 1/20 part of 0.5% potassium permanganate. In another non-limiting example, a solvent to fuel ratio of 6 parts denatured ethanol (including 2.5% water) to 1 part fuel can be used to differentiate, using 1/10 part of 0.5% potassium permanganate, between B20 (clear/yellow), B10 (cloudy/yellow), B2 (cloudy/peach), and between fuels contaminated with very low levels of biodiesel (e.g., B0.2), no biodiesel (e.g., ULSD), and high sulfur content diesel (e.g., 400 ppm sulfur content) (cloudy/purple).

The following EXAMPLES 5-8 provide examples of specific tests for reacting fuel with potassium permanganate to determine biodiesel content.

Example 5

Figure 6:
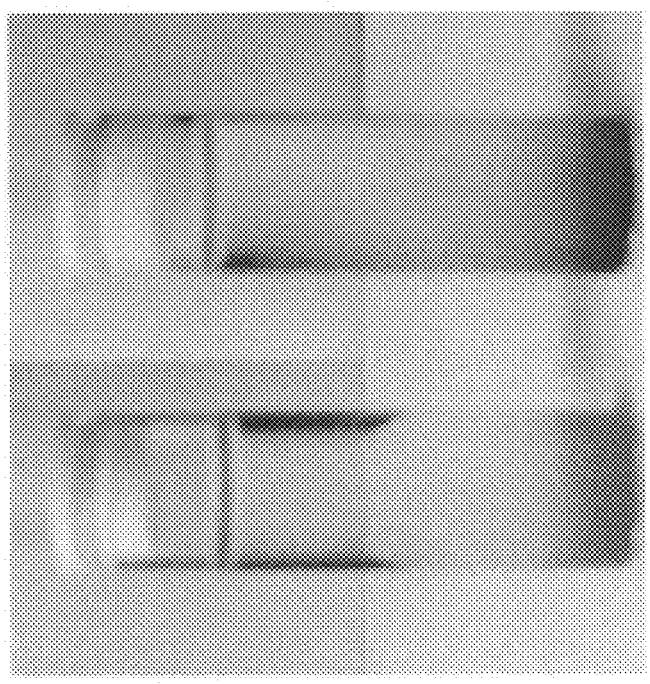
Figure 7:
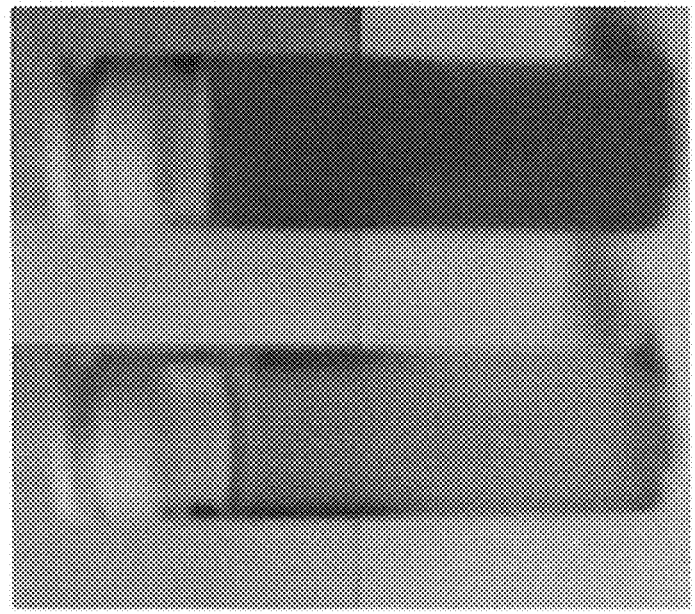

As shown in FIG. 6, one drop (0.025-mL) of 0.5% potassium permanganate decolorizes (or turns yellow) as it settles in a vial containing 0.5-mL B20 fuel and 3-mL of denatured ethanol (containing 5% methanol, 5% isopropanol and 90% ethanol) containing 2.5% distilled water. As shown in FIG. 7, after 2 seconds of shaking, the entire solution turns yellow. Decolorization is a result of the potassium permanganate reacting with denatured ethanol. One drop (0.025-mL) of 0.5% potassium permanganate remains purple as it settles in a vial containing 0.5-mL ULSD fuel and 3-mL of denatured ethanol (containing 5% methanol, 5% isopropanol and 90% ethanol) containing 2.5% distilled water, as shown in FIGS. 6 and 7.

Example 6

Figure 8:
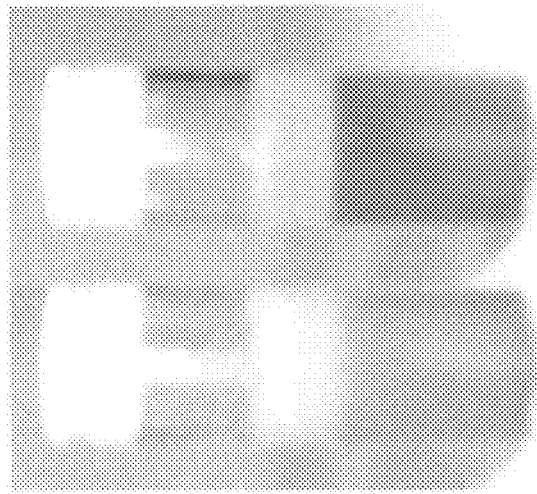

Using water in place of denatured ethanol under the same conditions listed above in EXAMPLE 5, the B20 lightens the potassium permanganate at a slow rate, as shown in FIG. 8 (after 1 minute).

Example 7

Figure 9:
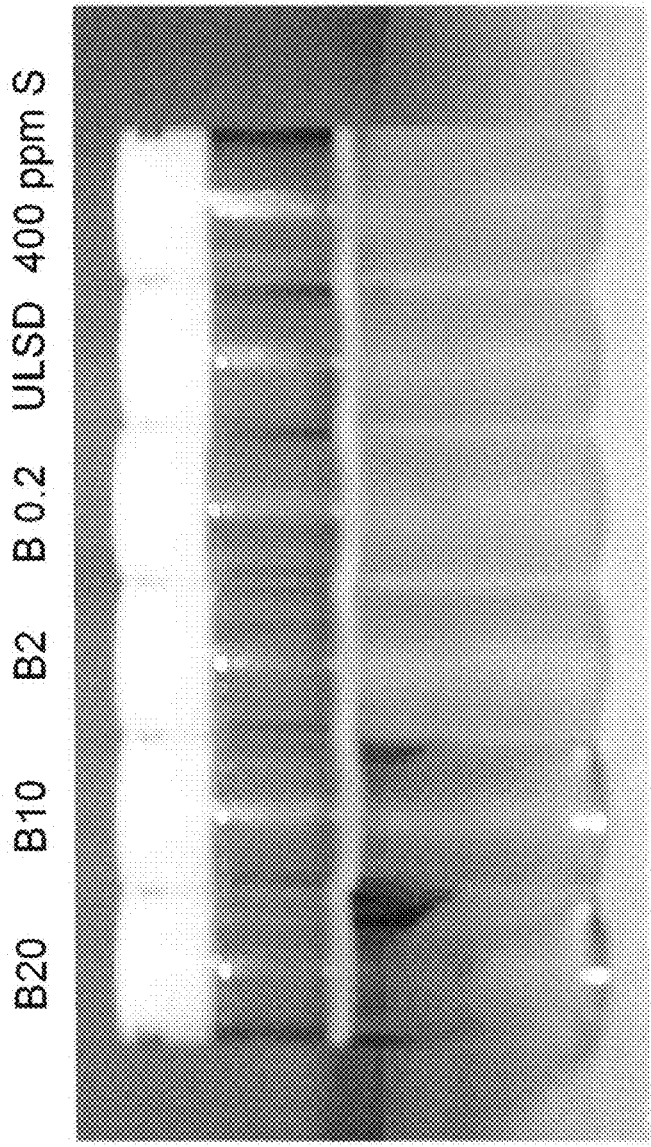
Figure 10:
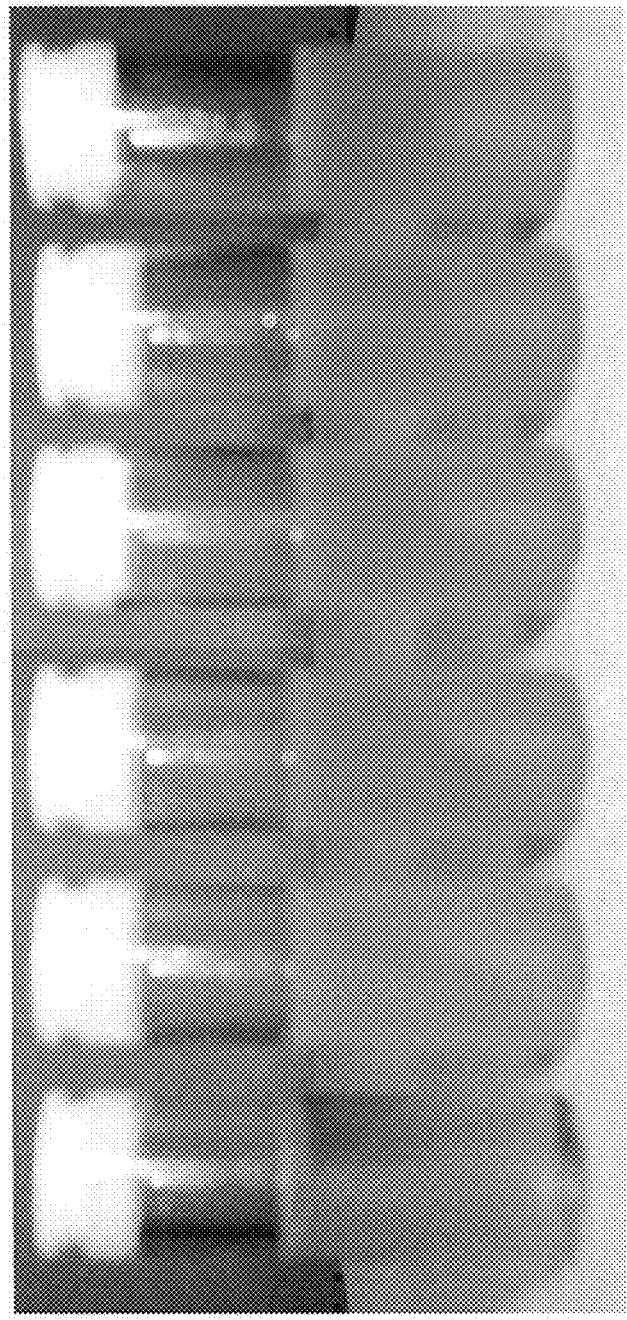

As an example of the combined solubility/potassium permanganate test, 0.5-ml samples of the following fuels were dispensed into 5-mL glass vials: B20, B10, B2 (2% biodiesel), B0.2 (0.2% biodiesel), ULSD fuel, and 400 ppm sulfur fuel. 3-mL of 2.5% water in denatured ethanol was then added to each vial. The vials were capped and shaken by hand for approximately 2 seconds. As shown in FIG. 9, the B20 and B10 fuel solutions were clear, while the other fuels were cloudy. Then 0.050-mL of 5% potassium permanganate was added to each fuel solution and shaken by hand for 2 seconds. As shown in FIG. 10, the B20 and B10 fuel solutions were yellow (B20 still clear), the B2 and 400 ppm sulfur fuels were peach, and the B0.2 and ULSD fuels remained purple in color. It should be appreciated that B2 and 400 ppm sulfur fuels can be differentiated from one another by the colorimetric sulfur test (B2 purple, 400 ppm sulfur decolorized). Therefore, the combined solubility/permanganate test can distinguish among B20 (clear/yellow), B10 (cloudy/yellow), and B2 (cloudy/peach) fuels, and between blended (B20 to B2) fuels and ULSD fuels contaminated with very low levels of biodiesel or high sulfur fuels (cloudy/purple).

Example 8

In a second test, the permanganate was added in an amount of 0.25-mL (instead of 0.050-mL) and was used to distinguish between B0.2 (cloudy/brown) and ULSD (cloudy/peach) fuels. There is a slight color difference between B0.2 and ULSD fuels due to difference in decolorization rates between the fuels.

The above EXAMPLES 5-8 provide examples of specific tests for reacting fuel with potassium permanganate to determine biodiesel content. ULSD fuels containing hydroperoxides also remained purple, indicating minimal reaction or interference of the hydroperoxides with the permanganate test.

Figure 11:
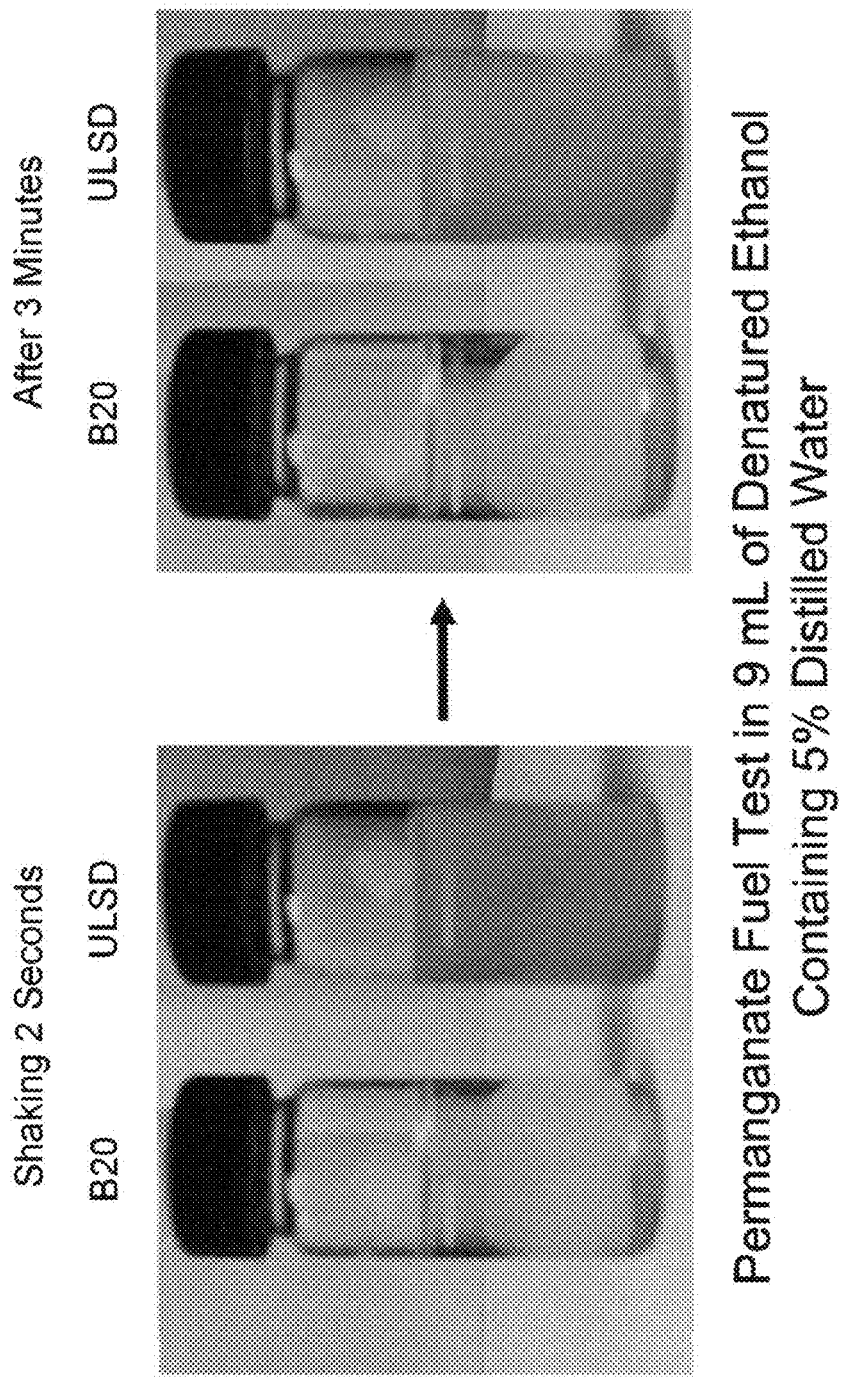
Figure 12:
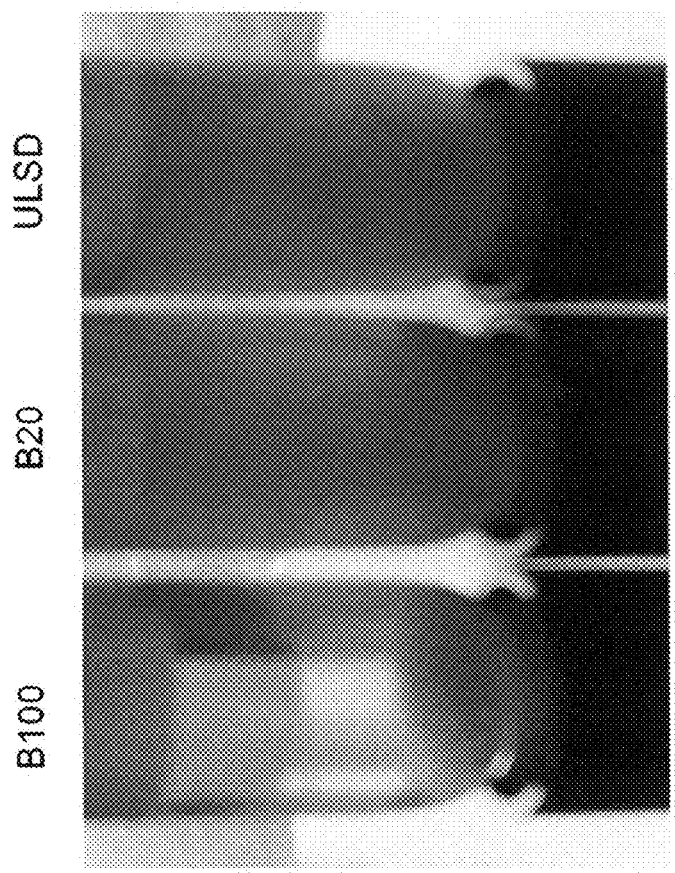

It should be further appreciated that the permanganate test should be performed quickly because after about 3 minutes all of the solutions turn brown as the permanganate oxidizes the denatured ethanol matrix, as shown in FIG. 11. Such oxidation is not a problem if water is used (see FIG. 8) in lieu of denatured ethanol; however, as mentioned above, the use of water requires two vials for separate solubility and permanganate tests. The time limitation on the solubility portion of the permanganate test is much less restrictive than the time limitation on the permanganate test, because B20 remains clear and ULSD remains cloudy after 2 seconds, as well as after 3 minutes, as shown in FIG. 11.

Saponification Test

The test for saponification in a basic, aqueous alcohol solution will now be described. Although the solubility and permanganate tests are suitable for rapid, on-site determinations of biodiesel content, their results are affected by the biodiesel molecular structure and the degree of unsaturation, respectively. Consequently, if a more accurate determination of the biodiesel concentration is required, then saponification reactions in basic, aqueous alcohol (such as ethanol) solutions can be performed because each biodiesel molecule contains one ester linkage.

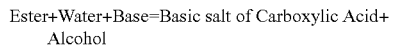

Ester+Water+Base=Basic salt of Carboxylic Acid+ Alcohol

If a known amount of base (e.g., potassium hydroxide, sodium phenoxide, etc.) is used to saponify a known amount of ester, then determining the difference in the moles of base before and after the ester reaction can be used to calculate the moles of reacted ester. Accordingly, in one embodiment of the present disclosure, the change to the fuel sample is saponification.

To perform the biodiesel test based on saponification, the following steps are performed in aqueous (limited reaction without water) basic ethanol:

(1) The concentrations of the carboxylic acids and hydroperoxides in the tested fuels, which rapidly react with the dissolved base, must be determined to obtain an accurate measurement of the biodiesel present in the ULSD. Therefore, 1-mL of fuel is mixed/stirred with an aqueous, basic ethanol solution containing potassium hydroxide (e.g., 0.1N) for approximately 1 minute. 10% of the reacted basic ethanol solution is then removed and titrated to an equivalence endpoint (pH indicator or electrode) with an aqueous, acidic ethanol solution containing hydrogen chloride (e.g., 0.01N). The difference between the moles of base in the basic ethanol solution before and after reaction with the fuel sample multiplied by 10 is used to calculate the moles of acid/acid number in the fuel sample.

(2) Assuming the fuel acid number is within the specifications of the fuel/engine manufacturer, then the remaining basic ethanol/fuel is allowed to sit overnight at room temperature or brought to its boiling point for 20 minutes to convert all of the biodiesel esters into their corresponding alcohol and potassium salt of the carboxylic acid. The difference between the moles of base remaining in the basic ethanol solution after the short-term reactions with the carboxylic acids and after the long-term saponification reaction with the fuel sample multiplied by 1.1 is equal to the moles of ester present in the biodiesel sample. If the average molecular weight of the biodiesel is known, then the moles of ester present can be converted into a percentage of biodiesel in the ULSD fuel.

If sodium phenoxide is used in place of potassium hydroxide, then the titration can be replaced by voltammetric analysis and performed in a vial without having to remove a portion for a separate acid titration. The fuel and basic aqueous ethanol are shaken in the vial for approximately 1 minute. The change in the sodium phenoxide concentration is determined with voltammetry (change dependent on acid concentration as described above without the 10 multiplication factor). The vial is then allowed to sit overnight and is reanalyzed by voltammetry to determine any additional change in the sodium phenoxide concentration (additional change dependent on ester content as described above without the 1.1 multiplication factor).

As an alternative to titration or voltammetric analysis, a set amount of base can be added to an aqueous ethanol solution (assumes acid content in ethanol solution is minimal), shaken for 10 seconds, then allowed to sit overnight. In the example shown in FIG. 11, phenolphthalein was used to indicate that excess base (pH>10) was still present: the left vial containing B100 is clear (fuel soluble) and colorless (all of the base neutralized by ester saponification—yellow due to fuel), while the middle and right vials containing B20 and ULSD fuels, respectively, are cloudy (fuel insoluble—B20 slightly less cloudy) and pink in color indicating that the amount of the base in the solution is still in excess (more base than ester. It should be appreciated that lowering the amount of initial base would allow B20 to turn colorless and be distinguishable from ULSD.

The following EXAMPLE 9 includes a sequence of steps for determining biodiesel content in fuel using all three tests described above: (1) solubility in an aqueous alcohol solution; (2) reaction with potassium permanganate in an aqueous alcohol solution; and (3) saponification in a basic, aqueous alcohol solution.

Example 9

To determine biodiesel content in fuel, an exemplary sequence follows.

Step 1. Solubility in denatured ethanol (containing 5% methanol, 5% isopropanol, and 90% ethanol) containing 2.5% of distilled water. If the solution is clear, the biodiesel concentration is greater than 10%. If the solution is cloudy, the biodiesel concentration is less than 10%.

Step 2. If the solubility test result is cloudy, add one drop (0.025-mL) of 0.5% potassium permanganate solution to solubility test vial. If the color changes from an initial purple color, the biodiesel concentration is greater than 0.2% (2000 ppm). Use standard fuels with color charts/colorimeter to estimate the percentage of biodiesel in the fuel sample. Interfering high sulfur fuels can be eliminated by using the colorimetric sulfur test.

Step 3. If final confirmation of biodiesel presence is required, take a new fuel sample and perform saponification in an aqueous basic solution (in boiling basic aqueous ethanol if needed in short-term, otherwise overnight test at room temperature).

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims. While illustrative embodiments have been illustrated and described, it will be appreciated that various changes can be made therein without departing from the spirit and scope of the disclosure.

The embodiments of the disclosure in which an exclusive property or privilege is claimed are defined as follows:

1. A method of analyzing biodiesel content in a fuel sample, comprising:
(a) providing a fuel sample including at least one of a biodiesel and other diesel fuel;
(b) mixing a predetermined amount of solvent with the fuel sample,
wherein the fuel sample is soluble in the solvent;

(c) mixing a predetermined amount of water with the fuel sample;
(d) analyzing the fuel sample for a change in clarity; and
(e) associating the change with a biodiesel content in the fuel sample.

2. The method of claim 1, wherein the other diesel fuel is selected from the group consisting of ULSD fuel, low sulfur diesel fuel, and regular sulfur diesel fuel.

3. The method of claim 1, wherein the solvent is selected from the group consisting of alcohols, low molecular weight ketones, esters, carboxylic acids, and nitriles.

4. The method of claim 1, wherein the change is detected by visual analysis.

5. The method of claim 1, wherein the solvent is isopropanol.

6. The method of claim 1, wherein the solvent is selected from the group consisting of denatured ethanol and water.

7. The method of claim 1, wherein the method includes mixing a predetermined amount of base with the fuel sample.

8. The method of claim 7, wherein the change is saponification.

9. The method of claim 1, further comprising adding a water and solvent soluble dye to the fuel sample.

10. The method of claim 9, wherein the dye is selected from the group consisting of methylene blue, Congo red, and food coloring.

11. The method of claim 10, further comprising adding a predetermined amount of potassium permanganate to the fuel sample.

12. The method of claim 11, wherein the change is a change in color.

13. A method of analyzing biodiesel content in a fuel sample, comprising:
    (a) providing a fuel sample including at least one of a biodiesel fuel and other diesel fuel;
    (b) adding a predetermined amount of solvent to the fuel sample, wherein the fuel sample is soluble in the solvent;
    (c) adding a predetermined amount of water to the fuel sample;
    (d) adding a predetermined amount of potassium permanganate to the fuel sample;
    (e) analyzing the fuel sample for a change in color, a change in clarity, and a combination thereof; and
    (f) associating the change of the fuel sample with a biodiesel content.

14. The method of claim 8, wherein the solvent is water.

15. The method of claim 8, wherein the other diesel fuel is ULSD fuel.

16. The method of claim 8, wherein the solvent is denatured alcohol.

17. The method of claim 13, wherein the change is detected by visual observation, a colorimeter, or a spectrophotometer.

* * * * *

UNITED STATES PATENT AND TRADEMARK OFFICE
CERTIFICATE OF CORRECTION

PATENT NO. : 7,927,877 B1  
APPLICATION NO. : 12/286845  
DATED : April 19, 2011  
INVENTOR(S) : R. E. Kauffman Page 1 of 1

It is certified that error appears in the above-identified patent and that said Letters Patent is hereby corrected as shown below:

| COLUMN | LINE | |
|---|---|---|
| 12 (Claim 14, | 20 line 1) | "claim 8" should read --claim 13-- |
| 12 (Claim 15, | 21 line 1) | "claim 8" should read --claim 13-- |
| 12 (Claim 16, | 23 line 1) | "claim 8" should read --claim 13-- |

Signed and Sealed this  
Sixth Day of September, 2011

David J. Kappos  
*Director of the United States Patent and Trademark Office*